United States Patent [19]

Homberg et al.

[11] 3,959,342

[45] May 25, 1976

[54] PROCESS FOR THE PREPARATION OF NITRILOTRIACETONITRILE (NTN)

[75] Inventors: Otto A. Homberg, Easton; Alan H. Singleton, Emmaus, both of Pa.

[73] Assignee: Bethlehem Steel Corporation, Bethlehem, Pa.

[22] Filed: Dec. 10, 1974

[21] Appl. No.: 531,273

Related U.S. Application Data

[63] Continuation-in-part of Ser. No. 66,255, Aug. 24, 1970, abandoned.

[52] U.S. Cl. ..................... 260/465.5 A; 260/534 E
[51] Int. Cl.² ........................................ C07C 120/00
[58] Field of Search ............................ 260/465.5 A

[56] References Cited
UNITED STATES PATENTS

| | | | |
|---|---|---|---|
| 2,205,995 | 6/1940 | Ulrich et al. | 260/465.5 A |
| 2,855,428 | 10/1958 | Singer et al. | 260/465.5 A |
| 3,061,628 | 10/1962 | Singer, Jr. et al. | 260/465.5 A |
| 3,337,607 | 8/1967 | Wollensak | 260/465.5 A |
| 3,504,011 | 3/1970 | Gandhi | 260/465.5 A |
| 3,679,728 | 7/1972 | Morgan et al. | 260/465.5 A |
| 3,679,729 | 7/1972 | Daniels | 260/465.5 A |
| 3,840,581 | 10/1974 | Neumaier et al. | 260/465.5 A |
| 3,856,844 | 12/1974 | Wikman | 260/465.5 A |
| 3,862,203 | 1/1975 | Greco et al. | 260/465.5 A |

Primary Examiner—Joseph P. Brust
Attorney, Agent, or Firm—Joseph J. O'Keefe; Charles A. Wilkinson; Michael J. Gilroy

[57] ABSTRACT

Nitrilotriacetonitrile (NTN) is produced in high yeilds from hydrogen cyanide, formaldehyde and ammonia, or its equivalent as an ammonium salt of a strong acid, by utilization of a critical two-stage reaction sequence within a narrow dilution ratio and temperature range. The reaction sequence steps provide for a first mixture to be prepared comprising a mixture of the formaldehyde and ammonia. No external adjustment of the pH of this mixture is permitted. A second mixture is prepared comprised of the HCN in an aqueous solution and a strong mineral acid such as sulfuric acid for adjusting the pH of the mixture to about 1 or less. NTN is produced by combining the mixtures at a temperature of from about 55° C. to about 70° C. either by adding the formaldehyde/ammonia solution to the HCN/acid solution or vice versa. The ratios and dilution of the reactants is critical for good yields. The aqueous solution of formaldehyde and ammonia or ammonium salt (calculated as ammonia) may have a ratio of total solute weight to solution weight within a range of about 25 to 60%, and an optimum mole ratio of formaldehyde to ammonia of no more than 3 to 1. In the combined mixtures a mole ratio of hydrogen cyanide to formaldehyde of 1.1 or greater and a concentration factor of total reactant weight to solution weight of from about 30 to about 40% is required.

The nitrilotriacetonitrile produced may be converted by hydrolysis to the carboxylic acid, nitrilotriacetic acid (NTA) or a carboxylic acid salt such as the sodium salt, known as SNTA. NTA and its salt are useful as detergent builders.

6 Claims, 1 Drawing Figure

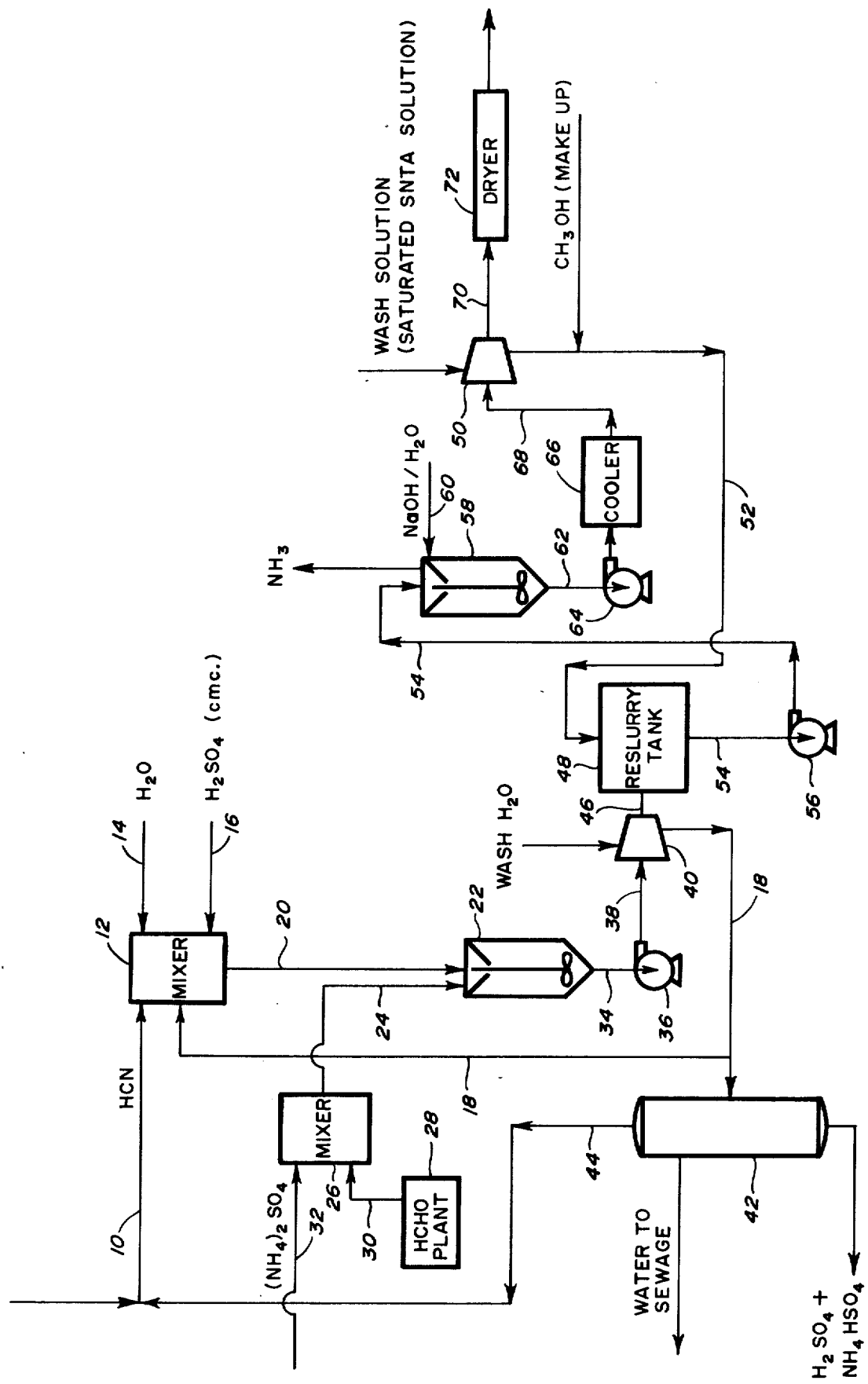

PROCESS FOR THE PREPARATION OF NITRILOTRIACETONITRILE (NTN)

Cross-References to Related Applications

This application is a continuation-in-part of application Ser. No. 66,255, filed Aug. 24, 1970, now abandoned.

Background of the Invention

This invention relates to a process for the preparation of nitriles and more particularly to carboxylic acid nitriles.

Prior art processes for the production of nitrilotriacetonitrile (NTN) from hydrogen cyanide, formaldehyde and ammonia are known. The reaction is known to take place at low pH's. Examples of these prior art processes include U.S. Pat. No. 3,337,607 to Wollensak, U.S. Pat. No. 2,885,428 to Singer et al. and U.S. Pat. No. 2,205,995 to Ulrich et al. The problems associated with NTN synthesis have persisted in that the high yields necessary to economically justify large scale production have eluded researchers despite the prodigious amount of work in this area. Prior art workers have attempted to resolve the problem of improvement of yields by the use of various techniques. For example, Ulrich et al in U.S. Pat. No. 2,205,995 ran a batch reaction in which ammonium sulfate was dissolved in formalin. HCL was added followed by sodium cyanide. Singer et al in U.S. Pat. No. 2,885,428 produces NTN by combining the formaldehyde solution, liquid HCN and sulfuric acid and adding thereto liquid ammonia at 50°-60° C. Wollensak, in U.S. Pat. No. 3,337,607 after a detailed explanation in which he duplicates Singer's experiment to shown its shortcomings, then discloses a method in which the formaldehyde and an ammonium salt are combined in aqueous solution and then HCN is added. A necessary low pH is preferably maintained in Wollensak by in situ generation of acid by a spontaneous hydrolysis of the ammonium salt but the reference also discloses that a mineral acid may be added to the reaction pot if desired. In spite of disclosures of Wollensak and others, the yields of NTN from these prior art processes remain unattractively low when applied to large scale production. A need exists for a process suitable for large scale use for the production of NTN which will provide high yields and still retain the benefit of inexpensive reactants.

Summary of the Invention

We have discovered a process for the preparation of nitrilotriacetonitrile in high yields which process is suitable for large scale production utilizing, as starting materials, hydrogen cyanide, formaldehyde and ammonia or its equivalent as a salt of a strong acid. The process of this invention includes a critical two stage mixing reaction sequence within a narrow dilution ratio, and produces nitrolotriacetonitrile, referred to hereinafter as NTN, according to the equation:

$$3H_2CO + NH_3 + 3HCN \rightarrow N(CH_2CH)_3 + 3H_2O \qquad (1)$$

Briefly, in the process of this invention, a first aqueous reaction mixture is prepared comprising the formaldehyde and ammonia. Ammonia as used herein means, inter alia, ammonia ($NH_3$) or its equivalent as the ammonium salt of a strong acid, such as ammonium chloride, ammonium sulfate, ammonium bisulfate and the ammonium acid phosphates, as is well known in the art. No external adjustment of the pH of this first mixture is permitted. A second separate mixture of the HCN in water is prepared and the pH of this second mixture is adjusted to about pH 1 or less by the use of a strong acid such as sulfuric acid, hydrochloric acid or the like as is well known in the art. NTN, is produced by combining the two mixtures either by adding the formaldehyde/ammonia mixture to the HCN/acid mixture, or vice versa, at from about 55° C. to about 70° C. The ratios and dilution of the reactants is critical for optimum formaldehyde to NTN conversion percentage. Nevertheless, such ratios and dilution factors may undergo moderate deviation from their preferred amounts with a resultant decrease in product yield based on formaldehyde consumed. It will be seen that, in the continuous process embodiment of this invention, infra, recycling steps for HCN and $NH_3$ are incorporated to optimize their utilization. In accordance with this recycling, these two reactants are kept in slight excess in the preferred embodiment such that formaldehyde conversion to NTN is optimized. Formaldehyde is selected as the base material with regard to which yield is optimized because under present economic conditions formaldehyde is the most expensive reactant. Under other economic conditions it might be preferable to optimize the yield based upon one of the other reactants, i.e. by using formaldehyde and the third reactant in slight excess. In any case by using the particular addition sequence of the invention the overall yield of NTN is very significantly increased over other addition sequences with otherwise similar reaction conditions. Thus, while the instant invention is described, infra, it its preferred form, moderate deviations from the reactant ratios cited are encompassed, which deviations result in less than optimum utilization of formaldehyde. Therefore, in the optimum embodiment of our process, the aqueous solution of formaldehyde and ammonia or ammonium salt (calculated as ammonia) must have a total solute to solution ratio by weight of about 25 to 60% and a mole ratio of formaldehyde to ammonia of no more than 3 to 1. In the combined mixtures a mole ratio of hydrogen cyanide to formaldehyde of 1.1 or greater, and a concentration factor of total reactant weight to solution weight of from about 30 to about 40% is required.

The NTN is produced as an aqueous slurry from which NTA, or preferably one of its soluble salts such as sodium nitrilotriacetate (SNTA) may be prepared by hydrolysis, as is well known in the art according to the equation:

$$N(CH_2CN)_3 + 3NaOH \rightarrow N(CH_2COONa)_3 + 3NH_3 \qquad (2)$$

By the use of the critical two stage mixing of this invention we have produced NTN in significantly higher yields than prior art processes. Our higher yields are surprising and unexpected in that the prior art understanding of the problem of low yield resulted from a singularly limited belief that while the pH of the reaction was critical, the method of providing the critical pH was immaterial. Thus the decision to add acid, in order to maintain a low pH, was based solely on the demands dictated by pot analysis of the on-going reaction within the reaction pot or vessel. Acid was therefore added directly to the reaction vessel, in which the formaldehyde, ammonia and hydrogen cyanide of the process were reacted, in response to the pH conditions monitored in the vessel. Thus, in accordance with this belief Wollensak, for example, was ultimately concerned only with continuing to regenerate a low pH as needed to off-set a natural trend toward higher pH's during the course of the reaction of equation (1). No other advantage of an acid pH except as required by the analysis of the pot was contemplated by the prior art. Thus, adding the acid required directly to the reaction pot prior to beginning the reaction, or constantly generating acid in situ as required, are exhaustive of the prior contributions to the art. We have discovered, however, that a particular combination comprising addition of a strong mineral acid, such as, for example, hydrochloric or sulfuric acid mixed with the hydrogen cyanide to another mixture of formaldehyde and ammonia or vice versa produces very superior high yields. That is, we have discovered that it is not simply sufficient that the reaction pot pH be kept low, but also that if this pH is achieved by adding the two acids, i.e. the HCN and the strong mineral acid, as one mixture with the other reactants as another mixture, significantly higher yields are achievable. By following the process of this invention we have been able to improve yields over any and all of the prior art addition sequences previously used by those skilled in the art in the production of NTN.

The following detailed description includes a general discussion of the preferred mode of operation of the process. Exemplary embodiments include a large scale process as referred to in the drawing, wherein NTN may be produced in a continuous method and which embodiment includes hydrolysis to SNTA. Also included are variations contemplated within the scope of this invention and a comparison of the process of our invention with those processes disclosed by the prior art to illustrate the advantages gained by employment of our method.

Brief Description of the Drawing

The FIGURE shows a schematic representation of the steps in a continuous process for the manufacture of SNTA from NTN produced by the process of this invention.

Detailed Description

A preferred mode by which our invention may be practiced is as follows: One and eleven hundreds (1.11) equivalents of formaldehyde, as a 37% aqueous solution known commercially as Formalin, is placed together with 0.4 equivalents of ammonium ion, as the sulfate, in a standard reaction vessel fitted with a stirrer assembly, thermometer, addition funnel and heating mantle. The contents are heated to 35°–40° C. with stirring. One hundred grams of water, 0.06 equivalents of sulfuric acid and 1.24 equivalents of hydrogen cyanide are placed in the addition funnel. Addition of the contents of the funnel is begun at about 40° C. and the addition rate is controlled to give a gentle hydrogen cyanide reflux. The pot temperature is allowed to gradually climb to between about 55° C. and 70° C. Completion of the reaction is invariably indicated by a separation of product at reaction temperature. At 64°–68° C. this separation usually occurs within about 15 minutes of reaching this temperature. Tests indicated no advantage could be demonstrated for maintaining the reaction temperature for more than 30 minutes. Laboratory tests of the mother liquor showed maximum product recovery could be accomplished by cooling the reaction mixture to less than 25° C. and stirring at this temperature for 30 minutes.

While laboratory size reactions are definitive and useful as a means of comparison of techniques and prior art processes, as will be demonstrated infra, a more useful example of a large scale production of NTN by our process is also easily performed. Since NTN is most often utilized as a precursor for sodium nitrilotriacetate, (SNTA) the continuous process of this invention will usually include, as a continuation of the nitrile reaction, a hydrolysis step for converting the NTN to SNTA.

Referring now to the FIGURE, anhydrous liquid hydrogen cyanide in line 10 is fed into mixer 12 at a rate of 6.7 kilograms/hour (Kg/hr.) to be combined there with water from line 14, sulfuric acid from line 16 and recycled mother liquor from line 18. The sulfuric acid addition is monitored by testing the pH of the mixture entering the reactor 22 and adjusting the rate of addition to keep the pH of the contents of the mixer below about 1. The materials in mixer 12 enter reactor 22 by line 20. Reactor 22 is also fed by line 24 which carries a preformed mixture of ammonium sulfate (5.25 Kg/hr.) from line 32 and formaldehyde (6.0 Kg/hr.) in 10.2 Kg/hr. of water from mixer 26. The formaldehyde is supplied to mixer 26 by generator 28 via line 30, and ammonium sulfate is supplied via line 32. The total rate of return of mother liquor and incoming fresh water from line 14 are adjusted so that the reactant weight is kept at about 36% of the solution weight in reactor 22.

The residence time in the reactor is about 45 minutes. A slurry of nitrilotriacetonitrile is formed in the reactor, and is withdrawn at line 34 and pumped by pump 36 via line 38 to a centrifuge 40, where most of the solid nitrile is separated from the slurry liquor. A portion of this separated liquor is recycled, via line 18 and mixer 12 to reactor 22, the remainder being directed to distillation column 42, where a certain amount of hydrogen cyanide (2.0 Kg/hr.) is recovered and mixed, via line 44, with fresh hydrogen cyanide entering the system at line 10. The wet nitrilotriacetonitrile is transferred from centrifuge 40 via line 46 and introduced into reslurry tank 48, where mother liquor from centrifuge 50, via line 52, is added to reform a slurry which is pumped by pump 56, via line 54, to reactor 58.

The nitrile (7.6 Kg/hr.) as a 25–33% (weight) slurry in mother liquor from centrifuge 50 (a saturated SNTA solution in a solvent containing about 60% methanol and about 40% water) and a 50% (weight) solution of sodium hydroxide in water (13.6 Kg/Hr.) are pumped continually into reactor 58 via lines 54 and 60, respectively. The reactor contents are maintained under reflux at about 70° C. by the heat evolved during the course of the exothermic reaction. Any suitable conventional heating and/or cooling means, not shown, may be arranged about reactor 58 such that the temperature may be confined to about 70°. A product stream is removed via line 62, in order to maintain a constant level in the reactor. The reactor is sized so as to accomodate a one hour residence time. The ammonia (2.9 Kg/hr.) which evolves during the reaction is collected in a purifying unit, not shown. The reaction mixture, leaving reactor 58 via line 62, is pumped by pump 64, to cooler 66, where the mixture is cooled to about 35° C. The cooled mixture then enters centifuge 50 by way of line 68, where the mother liquor is removed, the product being washed simultaneously with a small amount of saturated aqueous sodium nitrilotriacetate solution. The mother liquor and wash solution are recycled, via line 52, to reslurry tank 48. The product is then transferred, via line 70, to a drier 72, from which it is withdrawn as a dry monohydrate of sodium nitrilotriacetate (SNTA, 15.2 Kg/hr.)

In order to demonstrate the advantages of the process of this invention, the two-stage mixing step disclosed herein was compared with other mixing combinations. In order to verify that the changed yields are the product of our novel mixing order, all other factors, i.e. reactants, temperature, reaction completion and product recovery, were held constant from experiment to experiment. Furthermore, the conditions chosen were selected, as will be discussed below, to maximize the yields from the prior art processes so that a true evaluation of the maximum potential of our reaction method would be shown.

The reactants selected for the comparative tests were formaldehyde, as a 37% aqueous solution (Baker Analyzed Grade Formalin), HCN, as an anhydrous liquid, concentrated sulfuric acid (18 molar) and ammonium sulfate (Baker Analyzed Grade).

Since it is imperative in comparison work, especially in organic chemical reactions, to eliminate or stabilize variables which might influence the results, the following parameters for the comparative tests were developed:

Temperature

Tests showed that the optimum reaction temperature is between 64° C. to 68° C., with a range of 55° C. to about 70° C. being suitable. This temperature is readily attainable by controlling the mixing of the various reagents so that the heat evolved during the exothermic reaction is sufficient to produce a gentle hydrogen cyanide reflux until the desired pot temperature is reached. Therefore, all additions in comparative tests commenced at 35°–40° C. (reflux for HCN containing mixtures) and were maintained at gentle pot reflux temperature which gradually ranged upward with the changing pot concentrations.

Reaction Completion

Completion of the reaction is invariably indicated by a separation of product at the reaction temperature. At 64°–68° C. this generally occurred within 15–30 minutes of reaching this temperature. Tests indicated no advantage could be demonstrated for maintaining the reaction temperature for more than 30 minutes. Therefore, approximately 30 minutes constitutes maximum reaction yields, and was accordingly used as the time of reaction in all comparative tests.

Product Recovery

Tests of the mother liquor showed maximum product recovery was accomplished by cooling the reaction mixture to less than 25° C. and stirring at this temperature for 30 minutes. In the absence of this post-cooling stirring, additional product occasionally separated from the mother liquor after product isolation. Therefore, all comparative experiments included product recovery utilizing cooling to less than 25° C., with stirring, for about 30 minutes.

The results are summarized in Table I. In Table I, column I describes the mixing order, column II indicates the number of tests run and column III gives the weight percent yield and column IV gives the average of column III for each mixing order sequence, together with its standard deviation.

TABLE I

| I Method | II No. of Experiments | III Wt. % | IV Average |
|---|---|---|---|
| (1) Simultaneous mixing of all reactants | 5 | 48 | |
| | | 46 | |
| | | 52 | |
| | | 54 | |
| | | 53 | 51±2.8* |
| (2) Singular addition of formaldehyde | 2 | 55 | |
| | | 46 | 51±4.5* |
| (3) Singular addition of ammonium sulfate | 3 | 62 | |
| | | 65 | |
| | | 58 | 61±2.7* |
| (4) Addition of ammonium sulfate/ formaldehyde mixture | 10 | 76 | |
| | | 80 | |
| | | 78 | |
| | | 79 | |
| | | 79 | |
| | | 76 | |
| | | 77 | |
| | | 78 | |
| | | 81 | |
| | | 79 | 78±1.3* |
| (5) Singular addition of aqueous HCN | 2 | 70 | |
| | | 72 | 71±1* |
| (6) Addition of HCN/ Sulfuric Acid solution | 2 | 79 | |
| | | 75 | 77±2* |

*Standard Deviation quotations were calculated according to the formula:

$$S.D. = \pm \frac{\sum_{n-1}^{n} |\bar{x} - x_n|}{n}$$

where
 $x$ = individual experimental yield for each Method, $\bar{x}$ = average experimental yield for each Method
and
 $n$ = number of experiments As shown in Table I high yield of NTN is obtained only in Experiments 4 and 6 where the reactants are brought together in a two-stage process. In Experiments 4 and 6 there is a first preliminary mixing of the ammonium sulfate with the formaldehyde and the hydrogen cyanide with the sulfuric acid and a second stage where these two first mixtures are brought together and reacted. These results contrast with the prior art methods which correspond to Experiment 3 and 5.

Thus Table I indicates that, to achieve the high yields of this method the mixing order of reactants is critical. Experiments also established that the aqueous solution of formaldehyde and ammonia or ammonium salt (calculated as ammonia) must have a total solute weight to solution weight within the ratio of about 25 to 60%, an equivalent ratio of formaldehyde to ammonia of no more than 3 to 1, a mole ratio of hydrogen cyanide to formaldehyde of 1.1 or greater and a concentration factor of total reactant weight to solution weight of from about 30 to 40% in order to promote maximum product yields based on formaldehyde consumption.

There are also many variables contemplated within the scope of this invention.

Referring again to the drawing, in the nitrilotriacetonitrile reactor 22, the temperature should be held between 55° and 70° C. for efficient operation, 64° C. to 68° C. being optimum. Above 70° C., the yield of nitrilotriacetonitrile is low, due to decomposition of the reaction product.

When mother liquor from the nitrilotriacetonitrile slurry is recycled to reactor 22, via line 18, vessel 12 and line 20, the nitrilotriacetonitrile yield increases over the yield obtained with water only as the reaction medium. The increased yield is especially significant when the recycled mother liquor represents at least 30% of the weight of the reaction medium. Such increased yield may result from either or both of two independent factors. The first such factor is that the mother liquor is saturated with NTN such that, when used as the new reaction medium, NTN losses due to solubility in the solvent will be reduced. The second factor is that, there will remain in the mother liquor some stable intermediate products which, when recycled and exposed to additional reactants, will react to form the desired end product, NTN.

While ammonium sulfate and sulfuric acid have been used in the detailed example in reactor 22, ammonia, or any ammonium salt of a strong acid such as sulfuric, hydrochloric or phosphoric may be used in conjunction with a compatible strong acid. When ammonia is substituted, it is advisable to form the mixture with formaldehyde at or near the boiling point of the solution in tank 28.

In reactor 22, the weight ratio of the reactants, i.e. formaldehyde, ammonium compound and hydrogen cyanide, as may be determined from the specific example given above, is considered optimum for efficient operation. However, it is not necessary that the ratio be adhered to strictly. For example, a considerable excess of hydrogen cyanide is permissible.

In reactor 58 the reaction temperature, is controlled largely by the boiling point of the reaction media and rate of ammonia evolution.

It is possible to combine the reaction in reactor 22 and the reaction in reactor 58 in one reaction vessel. However, performing the reactions separately, as shown in the drawing provides a higher yield of substantially pure end product by permitting greater use of recycling and washing.

It is now possible, utilizing the invention thus described, to produce nitrilotriacetonitrile from inexpensive starting materials by a simple process suitable for a large scale production method which results in high yields, thus rendering NTN economically attractive.

We claim:
1. A process for the preparation of nitrilotriacetonitrile comprising:
   a. preparing a first aqueous solution of formaldehyde and at least one member selected from the group consisting of ammonia and ammonium salts of strong mineral acids, which solution contains no other components which would affect the pH of said solution;
   b. preparing a second aqueous solution of hydrogen cyanide and a strong mineral acid wherein the strong mineral acid is present in an amount precalculated to maintain the pH of the reaction of subparagraph (c) at a pH of about one or less;
   c. reacting said first aqueous solution with said second aqueous solution by combining said first aqueous solution and said second aqueous solution at a temperature from about 35° C to about 70° C.

2. The process according to claim 1 wherein in step (a) the mole ratio of formaldehyde to ammonia is 3:1 or less, and the ratio of total solute weight to total solution weight is within the range of about 25 to about 60%.

3. The process according to claim 1 wherein in step (c) the reaction mixture has a concentration factor of total reactant weight to total solution weight within the range of about 30 to about 40% and a mole ratio of hydrogen cyanide to formaldehyde of 1.1 or greater.

4. A process for the preparation of nitrilotriacetonitrile comprising:
   a. preparing a first aqueous solution of formaldehyde and at least one member selected from the group consisting of ammonia and ammonium salts of strong mineral acids, which solution contains no other components which would affect the pH of said solution, wherein the mole ratio of formaldehyde to ammonia is less than about 3 to 1, and the ratio of total solute weight to total solution weight is within the range of about 25 to 60%;
   b. preparing a second aqueous solution of hydrogen cyanide and a strong mineral acid wherein the strong mineral acid is present in an amount precalculated to maintain the pH of the reaction of subparagraph (c) at a pH of about 1 or less;
   c. reacting said first aqueous solution with said second aqueous solution by combining said first aqueous solution and said second aqueous solution at a temperature of from about 35° C to about 70° C and wherein the reaction mixture has a concentration factor of total reactant weight to total solution weight within the range of about 30 to about 40% and a mole ratio of hydrogen cyanide to formaldehyde of 1.1 or greater.

5. A process according to claim 4 wherein a portion of the mother liquor centrifugate from the nitrilotriacetonitrile product slurry derived from the reaction of paragraph 4(c) is recycled to the reaction vessel such that said mother liquor represents a portion of the weight of the reaction medium solvent for said reaction of paragraph 4(c).

6. A process according to claim 5 wherein the recycled mother liquor represents at least 30% of the weight of the reaction medium solvent for the reaction paragraph 4(c).

* * * * *